US006518481B1

(12) United States Patent
Wimmer et al.

(10) Patent No.: US 6,518,481 B1
(45) Date of Patent: Feb. 11, 2003

(54) UNIVERSAL MARKERS OF TRANSGENESIS

(75) Inventors: Ernst A. Wimmer, Bayreuth (DE); Andreas J. Berghammer, München (DE); Martin Klingler, München (DE)

(73) Assignee: Exelixis, Inc., South San Francisco, CA (US)

( * ) Notice: Subject to any disclaimer, the term of this patent is extended or adjusted under 35 U.S.C. 154(b) by 0 days.

(21) Appl. No.: 09/373,129

(22) Filed: Aug. 12, 1999

(51) Int. Cl.$^7$ .................. A01K 67/00; C12N 15/00; C12N 15/63; C12N 15/74; C07H 21/04

(52) U.S. Cl. .................. 800/13; 800/21; 435/320.1; 435/455; 435/473; 532/24.1

(58) Field of Search .................. 800/13–20, 21, 800/23, 251; 435/320.1, 455, 825, 473; 536/23.1, 24.1, 23.5

(56) References Cited

U.S. PATENT DOCUMENTS 6,135,942 A * 10/2000 Leptin .................. 536/23.1

OTHER PUBLICATIONS

Ngo et. al.; Computational Complexity, Protein Structure Prediction, and the Levinthal Paradox, 1994. In The Protein Folding Problem and Tertiary Structure Predicton (Merz, K. Jr. et al., eds) Birkhauser, Boston, pp. 491–494.*
A. Handler et.al.; The Lepidopteran transposon vector, piggyBac, mediates germ–line transformation in the Mediterranean fruit fly, Jun. 1998; Genetics, vol. 95, 7520–7525.*
T. Loukeris et.al.; Gene Transfer into the Medfly, Ceratitis capitata, with a Drosophila hydei Transposable Element; Dec. 1995, Science vol. 270, 2002–2005.*
E. Lozovskaya, et.al.; Germline Transformation of Drosophila virilis Mediated by the Transposable Element hobo, Jan. 1996; Genetics 142: 173–177.*
C. Coates et.al.; Mariner transposition and transformation of the yellow fever mosquito, Aedes aegypti, Mar. 1998, Genetics vol. 95., 3748–3751.*
N. Jasinskiene et.al.; Stable transformation of the yellow fever mosquito, Aedes aegypti, with the Hermes element from housefly; Mar. 1998, Genetics, vol. 95, 3743–3747.*
T. Loukeris et.al.; Introduction of the transposable element Minos into the germ line of Drosophila melanogaster, Oct. 1995, Genetics, vol. 92; 9489–9489.*
Moses, K. et al. Glass Encodes a Site–Specific DNA–Binding Protein that is Regulated in Response to Positional Signals in the Developing Drosophila Eye. Genes & Development 5:583–593, 1991.*
Peters, K.G. et al. Green Fluorescent Fusion Proteins: Powerful Tools for Monitoring Protein Expression in Live Zebrafish Embryos. Developmental Biology 171;252–257, 1995.*

Plautz, J.D. et al. Green Fluorescent Protein and its Derivatives as Versatile Markers for Gene Expression in Living Drosophila Melanogaster, Plant and Mammalian Cells. Gene 173:83–87, 1996.*
Yeh, E. et al. Green Fluorescent Protein as a Vital Marker and Reporter of Gene Expression in Drosophila. Proceedings of the National Academy of Science USA 92:7036–7040, Jul. 1995.*
Zhuo, L. et al. Live Astrocytes Visualized by Green Fluorescent Protein in Transgenic Mice. Developmental Biology 187:36–42, 1991.*
Strojek, R.M. et al. The Use of Transgenic Animal Techniques for Livestock Improvement. Genetic Engineering: Principles and Methods 10:221–246, 1988.*
Kappel, C.A. et al. Regulating Gene Expression in Transgenic Animals. Current Opinion in Biotechnology 3:548–552, 1992.*
Wall. R.J. Transgenic Livestock: Progress and Prospects for the Future. Theriogenology 45:57–68, 1996.*
Mullins, L.J. et al. Transgenesis in Rats and Larger Mammals. Journal of Clinical Investigations 98(11):S37–S40, 1996.*
Ebert, K.M. et al. A Moloney MLV–Rat Somatotropin Fusion Gene Produces Biologically Active Somatotropin in a Transgenic Pig. Molecular Endocrinology 2:277–283, 1988.*
Houdebine, L.–M. Production of Pharmaceutical Proteins from Transgenic Animals. Journal of Biotechnology 34:269–287, 1994.*
Hammer, R.E. et al. Genetic Engineering of Mammalian Embryos. Journal of Animal Science 63:269–278, 1986.*
Berghammer et al. 1999, Nature 402, 370–371.
Xu et al. 1999, Development 128, 383–395.
Sheng et al. 1997, Genes & Development 11, 1122–1131.
Database Biosis Online! Biosciences Information Service, Philadelphia, PA, US; BM Sanger et al. Accession No. PREV199800239202 abstract & IOVS Mar. 15, 1998, vol. 39(4) p. S47.

* cited by examiner

Primary Examiner—Remy Yucel
Assistant Examiner—Quang Nguyen
(74) Attorney, Agent, or Firm—Richard Aron Osman

(57) ABSTRACT

The invention relates to methods, cells and nucleic acids for making transgenic animals. The methods generally comprise introducing into a genome of an animal a genetic construct comprising a transcriptional regulatory element operably linked to a heterologous marker gene encoding a marker, wherein the element drives expression of the marker across genera transgenic in the construct sufficient to visually detect the marker in photoreceptive cells or organs, and selecting for transgenesis by visually detecting the marker in a photoreceptive cell or organ of the animal.

41 Claims, No Drawings

UNIVERSAL MARKERS OF TRANSGENESIS

INTRODUCTION

1. Field of the Invention

The field of the invention is markers for identifying transgenic animals.

2. Background of the Invention

Genetic manipulation of insects and other arthropods is a highly desirable goal for the development of better control strategies to fight agricultural pests and disease vector species. Transposon-based transformation techniques had been available for Drosophila, but only recently did the discovery of new transposons enable this approach in other insects (O'Brochta & Atkinson, 1996, Insect Biochem. Molec. Biol. 26, 739–53), i.e medflies (Loukeris et al., 1995, Science 270, 2002–5; Handler et al., 1998, PNAS 95, 7520–5) and mosquitoes (Coates et al., 1998, PNAS 95, 3748–51; Jasinskiene et al., 1998, PNAS 95, 3743–7). However, a major obstacle in the use of these transposons has been the difficulty to obtain marker genes that allow easy and reliable identification of transgenic animals. In fact, a main reason why germline transformation experiments have not been carried out routinely so far in non-dipteran insects, is the lack of specific markers to follow gene transfer (DeVault et al., 1996, Genome Research 6, 571–9). Here we present a novel marker system broadly suitable for eye-bearing animals.

In combination with a set of promiscuous vectors, our system permits the study of biologically relevant questions in almost any species, not only in established model organisms. Since the very same system can be used in a series of different organisms, comparative biological and functional evolutionary studies are facilitated, providing a vital tool for the emerging field of evolutionary developmental biology. Furthermore, expression in the eyes allows visualization of the signal in animals with non-transparent cuticle, and transgenic animals can be identified as larvae, pupae and adults. Together with the fact that the system can be applied to competitive wild type strains rather than potentially labile mutant lines, makes the system particularly applicable to pest management programs.

SUMMARY OF THE INVENTION

The subject methods generally comprise (a) introducing into a genome of an animal a genetic construct comprising a transcriptional regulatory element operably linked to a heterologous marker gene encoding a marker, wherein the element drives expression of the marker across genera transgenic in the construct sufficient to visually detect the marker in photoreceptive cells or organs, and (b) selecting for transgenesis by visually detecting the marker in a photoreceptive cell or organ of the animal. In particular embodiments, the construct comprises a vector, such as transposon or retrovirus, particularly a polytropic vector. The construct may integrate into the genome by homologous or non-homologous recombination. In particular embodiments, the transcriptional regulatory element comprises a binding site selected from a Pax-6 binding site, a Glass binding site, etc., particularly a plurality of P3 sites, and the marker is a fluorescent protein, particularly a green fluorescent protein or variant thereof.

The subject compositions include polytropic vectors functional in nondipteran species and comprising a transcriptional regulatory element operably linked to a heterologous marker gene encoding a marker, wherein the element drives expression of the marker across genera transgenic in the construct sufficient to visually detect the marker in photoreceptive cells or organs, particularly wherein the marker is the only visually detectable indicator of transgenesis encoded by the vector. The invention also provides cells and animals transgenic in the subject constructs and/or made by the subject methods.

DETAILED DESCRIPTION OF PARTICULAR EMBODIMENTS OF THE INVENTION

The following descriptions of particular embodiments and examples are offered by way of illustration and not by way of limitation. Unless contraindicated or noted otherwise, in these descriptions and throughout this specification, the terms "a" and "an" mean one or more, the term "or" means and/or and polynucleotide sequences are understood to encompass opposite strands as well as alternative backbones. The subject methods and applications are applicable to a wide variety of photoreceptor cell or organ bearing animals. By photoreceptive cells or organs is meant any light sensing cell or organ of an animal and include cells such as simple pigmented light sensitive cells or retinular cells and structures such as ocelli also called simple eyes or eye spots like the direct or inverted pigment cups of many worms, structures such as compound eyes found in many arthropods, structures such as complex eyes or camera eyes of cephalopod molluscs and vertebrates. Unless otherwise noted, the term eye is used herein to collectively refer to these various light sensing cells or organs. The suitability of any particular photoreceptor cell or organ bearing animal is readily determined empirically, using conventional genetic transformation procedures and screening procedures, as exemplified below. Genera demonstrating transgenesis according to the disclosed methods include vertebrates, particularly mammals, fish and birds, and non-arthropod and arthropod invertebrates, such as Crustacea, Chelicerata and Insecta, such as Diptera such as flies and mosquitoes, and non-dipteran insects, such as Lepidoptera, Hymenoptera, Coleoptera, Neuroptera, Hemiptera, Isoptera, Dictyoptera, and Orthoptera.

The subject methods employ a transcriptional regulatory element operably linked to a heterologous marker gene encoding a marker, wherein the element drives expression of the marker across genera transgenic in the construct sufficient to visually detect the marker in photoreceptive cells or organs. By drives expression across genera is meant that the element is capable of promoting gene expression in a plurality of genera, preferably including a non-dipteran insect, more preferably including a non-insect arthropod. Preferred elements are functional in a plurality of taxonomic (Zoological Record, BIOS UK, 1999) families, preferably a plurality of orders, more preferably a plurality of classes, more preferably a plurality of phyla. In particular embodiments, the element is functional in at least the families Drosophilidae, Calliphoridae and Culicidae, preferably in the orders Diptera, Lepidoptera and Coleoptera, more preferably in the classes Insecta, Malocostraca and Chelicerata, even more preferably across the phyla Arthropoda, Mollusca and Chordata.

To drive marker expression in a series of diverged organisms requires a promoter which is active in a wide range of species. Furthermore, to avoid problems with low expression and the interference of autofluorescence, a regional specific promoter is preferable over a constitutively active one. A wide variety of regulatory elements may be employed, so long as they meet the requisite functional limitations. These may be natural promoter elements, naturally driving gene expression in photoreceptive cells or organs, elements derived from such natural promoter elements by mutational selection or consensus sequences, synthetic elements derived by iterative selection process, e.g. SELEX procedures, etc. In a particular embodiment, the element comprises a binding site selected from a Pax-6, a Pax-6 like binding site such as a twin-of-eyeless (TOY) binding site, a Glass binding site, etc. In more particular embodiments, the element comprises a Pax-6 Paired Domain or Homeodomain binding site, more particularly a P3 site, wherein the P3 site comprises the sequence: TAATYNRATTA (SEQ ID NO:01), wherein Y=C or T; R=G or A; N=any nucleotide (Wilson et al., 1993, Genes Dev 7, 2120–34; Czerny and Busslinger, 1995, Mol Cell Biol 15, 2858–71). Tables 1–6 provide other exemplary transcriptional regulatory element binding sites functional in the subject methods. Pax-6 binding sites are of particular interest due to the evolutionary conserved role Pax-6-homologs play in eye development across different phyla (Callaerts et al., 1997, Annu Rev Neurosci 20, 483–532).

TABLE 1

Natural promoter/enhancer elements 1. alpha A-crystallin promoter element, Cvekl et al., 1995, Mol Cell Biol 15, 653–60.
2. delta I-crystallin enhancer element, Cvekl et al., 1995, PNAS 92, 4681–5.
3. zeta-crystallin promoter element, Richardson et al., 1995, PNAS 92, 4676–80.
4. QP1, QPB1 and QPB2 sites, Plaza et al., 1995, Mol Cell Biol 15, 3344–53.
5. PBS site, Holst et al., 1997, PNAS 94, 1465–70.
6. 212 bp ey intron enhancer, Hauck et al., 1999, PNAS 96, 564–569.
7. HPD of L1 gene, Meech et al., 1999, PNAS 96, 2420–2425.

TABLE 2

GMR (glass multimer reporter) comprised of a plurality of the following sites (Ellis et al., 1993, Development 119, 855-65; Hay et al., 1994, Development 120, 2121-9)

1. TCGAGCCCAGTGGAAACCCTTGAAATGCCTTTAAG (SEQ ID NO:02)
2. TCGACTTAAAGGCATTTCAAGGGTTTCCACTGGGC (SEQ ID NO:03)
3. GATCCCAGTGGAAACCCTTGAAATGCCTTTAA-(SEQ ID NO:04)
4. GATCTTAAAGGCATTTCAAGGGTTTCCACTGG-(SEQ ID NO:05)
5. TCGAGACACCCAGTGGAAACCCTTGAAATGCCTTTAACTATTG (SEQ ID NO:06)
6. TCGACAATAGTTAAAGGCATTTCAAGGGTTTCCACTGGGTGTC (SEQ ID NO:07)
7. TCGAGACACCCAGTGGAAACCCTTGAAATGCCTTTAACTCAGTG (SEQ ID NO:08)
8. TCGACACTGAGTTAAAGGCATTTCAAGGGTTTCCACTGGGTGTC (SEQ ID NO:09)
9. TCGAGACACCCAGTGGAAACCCTTGAAATGCCTTTTCAGATTG (SEQ ID NO:10)
10. TCGACAATCTGAAAAGGCATTTCAAGCGTTTCCACTGGGTGTC (SEQ ID NO:11)

TABLE 3

Naturally occurring Pax-6 P3 sites (Wilson et al., 1995, Cell 82, 709-19)

1. TAATCAGATTA (SEQ ID NO:12)
2. TAATTGAATTT (SEQ ID NO:13)
3. TAATTGGGTTA (SEQ ID NO:14)
4. TAATCCAATTC (SEQ ID NO:15)
5. TAATTGGCTCA (SEQ ID NO:16)
6. TAATCCAATTG (SEQ ID NO:17)
7. AAATTGAATTA (SEQ ID NO:18)
8. TAATTTAATTT (SEQ ID NO:19)
9. TAATATGATTA (SEQ ID NO:20)
10. TAATTGAATTA (SEQ ID NO:21)
11. TAATGTAATTA (SEQ ID NO:22)
12. TAATTCAATTA (SEQ ID NO:23)

TABLE 4

Paired domain; Pai- and Red-domain binding sites (Epstein. et al., 1994, Genes Dev 8, 2022-34; Jun and Desplan, 1996, Development 122, 2639-50; Jun et al. 1998, PNAS 95, 13720-5)

| | |
|---|---|
| ANNTTCACGCATGANT (SEQ ID NO:24) | ATGTTCACTGA (SEQ ID NO:31) |
| ANNTTCACGCTTCANT (SEQ ID NO:25) | TCACTGA |
| ANNTTCACGCATCANT (SEQ ID NO:26) | TTCACGG |
| ANNTTCACGCTTGANT (SEQ ID NO:27) | GTCACGC |
| ATGCTCAGTGAATGTTCATTGA (SEQ ID NO:28) | TTCACGC |
| TCAATGAACATTCACTGAGCAT (SEQ ID NO:29) | |
| GTCACGG | |
| TGCATCGAGG (SEQ ID NO:30) | |

TABLE 5

Paired domain (PD) and paired-type homeodomain co-sites
(Jun and Desplan, 1996, Development 122, 2639-50)

1. CAATTAGTCACGC (SEQ ID NO:32)
2. CAATTATTCACGC (SEQ ID NO:33)
3. CAATTAGTCACGG (SEQ ID NO:34)
4. CAATTATTCACGG (SEQ ID NO:35)
5. CGATTAGTCACGC (SEQ ID NO:36)
6. CGATTATTCACGC (SEQ ID NO:37)
7. CGATTAGTCACGG (SEQ ID NO:38)
8. CGATTATTCACGG (SEQ ID NO:39)

TABLE 6

Paired-type homeodomain P2 and P1/2 sites (Wilson et al., 1993, Genes Dev 7, 2120-34)

1. TAATTGATTA (SEQ ID NO:40)
2. TAATCGATTA (SEQ ID NO:41)
3. TAATCAATTA (SEQ ID NO:42)
4. TAATTG
5. TAATCG
6. TAATTAATTA (SEQ ID NO:43)

The strength and/or specificity of the element may often be enhanced by multimerizing the binding site, i.e. providing a plurality of binding sites within the element. The number of binding sites is readily optimized empirically and is generally from 3 to 9. The plurality may be directly linked or separated by spacer sequence of 1 bp to 1 kb, preferably fewer than 250 bp, more preferably fewer than 50 bp, which may be of any sequence compatible with the required functionality of the element. Exemplary spacers used herein include GAGAC, GAGC, and GGATCCAAGCTTATCGATTTCGAACCCTCGACCGCCGGAG (SEQ ID NO:44).

The element generally also comprises a basal RNA Pol II promoter, the core promoter site that generally contains a TATA box sequence and transcriptional initiation site, and which functions in conjuction with transcription enhancer functions provided in the subject elements by the transcription factor binding site regions. A wide variety of basal promoters may be employed in the elements so long as they facilitate, in conjunction with the binding site(s), the requisite transcriptional regulation. Exemplary basal promoter elements include those of the Drosophila hsp70 gene promoter and Adenovirus major late promoter (MLP).

A wide variety of multimeric and/or combinatorial binding site—spacer—basal promoter combinations may be used—essentially any combination functions in conjunction to provide the requisite transcriptional regulation. For best results we find 0 to 10 bp spacers between the binding sites provide optimal synergistic effect of the binding sites and a spacer of 20 to 40 bp should separate the binding sites from the basal promoter.

The construct includes a marker gene encoding a marker which, when expressed in the transgenic animal, is visually detectable in a photoreceptive cell or organ of the animal. Criteria for marker selection include detectability, physiological and method compatibility, e.g. smaller sized marker genes enable small transposon constructs resulting in high transformation rates. A wide variety of markers may be encoded, including ribozymes or protein enzymes such as galactosidase, luciferase (e.g. Wilson and Hastings, 1998, Annu Rev Cell Dev Biol 14, 197–230), etc., and particularly directly detectable proteins, more particularly fluorescent proteins, especially commercially available enhanced fluorescent proteins (e.g. EGFP, ECFP and EYFP, Clontech Laboratories, Inc.).

Fluorescent proteins may comprise naturally occurring, engineered (i.e., analogs) and/or synthetic sequences. For example, many cnidarians use natural green fluorescent proteins ("GFPs") as energy-transfer acceptors in bioluminescence. Natural GFPs have been isolated from numerous animals, including the Pacific Northwest jellyfish, *Aequorea victoria*, the sea pansy, *Renilla reniformis*, and *Phialidium gregarium*; Ward et al., Photochem. Photobiol., 35:803–808 (1982); Levine et al., Comp. Biochem. Physiol., 72B:77–85 (1982). In addition, a variety of Aequorea-related fluorescent proteins having useful excitation and emission spectra have been engineered by modifying the amino acid sequence of a naturally occurring GFP from *Aequorea victoria* (Prasher et al., Gene, 111:229–233 (1992); Heim et al., Proc. Natl. Acad. Sci., USA, 91:12501–04 (1994). Particularly useful are GFPs from or which derive from the jellyfish *A. victoria* (see e.g. U.S. Pat. No. 5,491,084 for applicable such GFPs) and include variants offering a variety of different excitation and emission wavelengths; see e.g. Heim and Tsein, 1996, Current Biology 6, 178–182. Exemplary amino acid variants include F64L, S65T, Y66W, N146I, M153T, V163A and N212K, and combinations thereof. For example, CFP is the GFP of *Aequorea victoria* with the following additional mutations: F64L, S65T, Y66W, N146I, M153T, V163A, N212K (Miyawaki et al., 1997, Nature 388:882–7), and YFP is the GFP of *A. victoria* with the following additional mutations: S65G, V68L, S72A, T203Y (Cubitt et al., 1999, Methods Cell Biol 58, 19–30). Accordingly, in preferred embodiments, the marker is a Aequorea or Aequorea-related fluorescent protein, see U.S. Pat. No. 5,912,137 for applicable sequence, scope, definitions and examples.

Suitable fluorescent proteins may also derive from other sources, and include the yellow fluorescent protein from *Vibrio fischeri* strain Y-1 (Baldwin et al., Biochemistry (1990) 29:5509–15) which requires flavins as fluorescent co-factors; Peridinin-chlorophyll, a red fluorescing binding protein from the dinoflagellate Symbiodinium sp. (Morris et al., Plant Mol Biol, (1994) 24:673:77); phycobiliproteins from marine cyanobacteria such as Synechococcus, e.g., phycoerythrin and phycocyanin (Wilbanks et al., J. Biol. Chem. (1993) 268:1226–35), yellow to red fluorescing proteins which require phycobilins as fluorescent co-factors.

The subject constructs may be introduced into the genome of the targeted animal by any convenient methods. A wide variety of transformation methods are widely known for and/or are adaptable to a wide variety of target animals. For example, many applications are amenable to direct injection of naked construct DNA. In other embodiments, the construct further comprises regions which provide homologous recombination and integration into a target site of the genome. In yet other embodiments, the constructs are incorporated in a vector, such as a transposon or retrovirus. A wide variety of vectors may be employed, as influenced by the nature of the construct and the targeted host. In more particular embodiments, the vector is polytropic (functional across multiple genuses) or pan tropic (functional across mutliple families, preferably classes, more preferably orders), a wide variety of which are well known in the art, including the following: (a) recombinant retroviruses for example Moloney murine leukemia virus-based vectors (here termed "MLV>VSVG") having the envelope protein of vesicular stomatitis virus substituted for the amphotropic envelope protein (Burns et al., In Vitro Cell Dev Biol Anim (1996) 32:78–84; Lin et al., Science (1994) 265:666–669; Lu et al., (1996) PNAS 93:3482–3486; Jordan et al., (1998) Insect Mol Biol 7:215–222; U.S. Pat. No. 5,670,354; WO9603034); (b) recombinant baculoviruses for example vectors based on Autographa Californica Nuclear Polyhedrosis Virus (AcNPV, U.S. Pat. No. 5,731,182) or recombinant AcNPV derived vectors also engineered to express the envelope protein of vesicular stomatitis virus (here termed "AcNPV>VSVG") (Barsoum et al.,1997, Hum Gene Ther 8:2011–2018); and (c) transposon based vectors for example Himar1, piggyBac, Hermes, hobo, minos, mariner, etc.

The constructs may also include a variety of other components as dictated by practical or experimental objectives. For example, in particular embodiments, the constructs contain one or more of the following elements:

(1) a "test gene" operably fused to a promoter whose function is to be assayed in the transgenic animal, e.g. as a possible biopesticide or pesticide target;

(2) a "product gene" operably fused to a promoter, which produces a useful product which can be isolated from transgenic animals, e.g. a modified silk gene or biopharmaceutical;

(3) a "transformation gene" operably fused to a promoter, which alters the physical or behavioral properties of transgenic animals in useful ways, e.g. a "pacification gene" which tames africanized bees or fire ants;

(4) a "promoter-less or enhancer-less reporter gene" for gene tagging and mutagenesis;

(5) a regulatable "enhancer" or "promoter" to drive expression of genes adjacent to the insertion site of the vector for misexpression analysis;

(6) a "DNA manipulation element" such as a recombinase action site (e.g. FRT or loxP sites) for engineering specific chromosomal rearrangements, insertions, or deletions in transgenic animals; and (7) an "insulator element" which protects transgenes from interfering regulatory effects or position effects of adjacent enhancers or silencers.

The contructs are introduced the target animal or cell genome by any convenitent method, as advised by the nature of the construct and target animal or cell; well-established methodologies include microinjection, electroporation, lipofection, biolistics and the like, and genome site integration may be targeted (e.g. by homologous recombination) or nontargeted. Following introduction of the construct into the target animal genome, the methods involve selecting for transgenesis by visually detecting the marker in a photoreceptive cell or organ of the animal. A variety of means may be used to detect the marker, depending on the marker, animal, requisite throughput, etc. Detection may be indirect, by detecting a colored or fluorescent catalytic product of the maker, or preferably, direct, by detecting a colored or fluorescent marker. As used herein, "visual detection", and variants thereof, means detecting changes in the emission or reflection of light by direct and/or indirect means including visual inspection, visual inspection enhanced by the use of an optical instrument such as a microscope, photographic or photochemical measurement, photoelectric measurement, etc. For example, detection may be facilitated by automated and/or robotic instrumentation such as fluorimeters, digital imaging spectroscopy (Delagrave et al., (1995) Biotechnology 13:151–154; Youvan et al., (1995) Methods Enzymol 246:732–748; U.S. Pat. No. 5,852,498), etc. Table 7 shows successful detection of markers of transgenesis pursuant to the subject methods.

TABLE 7

Exemplary transgenic expression-marker detection systems

| Vector | Element | Marker | Host | Expression |
|---|---|---|---|---|
| hobo | 3xP3-hsp70 TATA | EGFP | drosophila | ++++ |
| Hermes | 9xP2-hsp70 TATA | ECFP | tribolium | ++++ |
| piggyBac | 3x(P2+PD)-hsp70 TATA | EYFP | grasshopper | ++++ |
| Himar1 | 6x(P2+PD-hsp70 TATA | luciferase | zebrafish | ++++ |
| piggyBac | 3xP3-hsp70 TATA | EGFP | chicken | ++++ |
| MLV>VSVG | 3xP3-hsp70 TATA | EGFP | mouse | ++++ |
| AcNPV | 3xP3-hsp70 TATA | EGFP | human | ++++ |
| piggyBac | 3xP3-hsp70 TATA | EGFP | cockroach | ++++ |
| mariner | 3xP3-hsp70 TATA | EGFP | honeybee | ++++ |
| Hermes | 3xP3-hsp70 TATA | EGFP | mosquito | ++++ |
| piggyBac | 3xP3-hsp70 TATA | EGFP | shrimp | ++++ |
| Himar1 | 3xP3-Adeno MLP TATA | EGFP | lobster | ++++ |
| piggyBac | 3xP3-Adeno MLP TATA | EGFP | termite | ++++ |
| AcNPV>VSVG | 3xP3-Adeno MLP TATA | EGFP | bollworm | ++++ |
| piggyBac | 3xP3-Adeno MLP TATA | EGFP | fire ant | ++++ |
| minos | 3xP3-Adeno MLP TATA | EGFP | med. fly | ++++ |

DETAILED EXAMPLE OF THE INVENTION

Here we show that an artificial promoter combines the necessary criteria of being hyperactive, regionally restricted and polytropic. We used an artificial promoter containing three Pax6 P3 binding sites in front of a TATA box (3×P3). Our P3 site is an idealized (SELEX-derived) paired class homeodomain binding site (Wilson et al., 1993, Genes Dev 7, 2120–34) which in combination with the hsp70 TATA box (−40–+70) is sufficient to regulate photoreceptor cell-specific gene expression in Drosophila (Sheng et al., 1997, Genes Dev. 11, 1122–31). In combination with our marker that encodes an enhanced GFP variant, EGFP (Heim and Tsien, 1996; Tsien, 1998, Annu. Rev. Biochem. 67, 509–44), we can show that this regulatory element does not show any species specificity, and we have used it as a marker for transgenesis in insects of different orders.

We initially demonstrated that our 3×P3 promoter, having 3 P3 sites in front of the hsp70 TATA-box, could work with EGFP. We introduced P3×3-EGFP into the CaSpeR P-Element vector that carries a mini w+ (Thummel and Pirotta, Dros Inf Serv. 71, 150), and checked the resulting transformants, identified by their yellow to red eye color, for EGFP expression in the eyes. We found that the lighter the eye color, the better one could see the EGFP in the compound eyes. There was little difference in the ocelli. In flies with very dark eyes the EGFP could only be seen in the ommatidia one looks straight into, whereas in lightly colored eyes one could see the complete eye glowing. Moreover, we could actually detect more transgenic lines using the P3×3-EGFP marker than with the mini w+, which indicates that our marker is less affected by position effects and therefore more useful than mini w+.

We then constructed three vectors based on Hermes (Warren et al., 1994, Genetical Res. Camb. 64, 87–97), piggyBac (Cary et al., 1989, Virology 172, 156–169.) and mariner (Medhora et al., 1989, EMBO J. 7, 2185–2189) transposons, each carrying the 3×P3-EGFP marker. Together with appropriate helper plasmids providing the respective transposases (Handler et al., 1998, Proc. Natl. Acad. Sci. USA 95, 7520–25.; Coates et al., 1998, Proc. Natl. Acad. Sci. USA 95, 3748–3751.; Jasinskiene et al., 1998, Proc. Natl. Acad. Sci. USA 95, 3743–3747.), these vectors were microinjected into Drosophila eggs of a strain mutant for the white gene (vector and helper plasmids at 500 and 300 ng/µl, respectively). We obtained transgenic lines displaying strong fluorescence with a frequency of 4% for mariner, 50% for Hermes and 35% for piggyBac (transformation efficiency is measured as percentage of fertile injection survivors producing fluorescent offspring). In parallel, we microinjected the Hermes and piggyBac vectors into the posterior pole plasm of Tribolium eggs from a strain lacking eye pigmentation (pearl mutant). We obtained transgenic lines, with efficiencies of 1% for Hermes and 60% for piggyBac. The transgenes are stably integrated into the genome as they have been inherited over multiple generations. For both species, we found that the strong fluorescence is detectable even after outcrossing to wild type strains. This result shows that our marker can be detected also in the presence of eye pigments. Moreover, in both species all photoreceptor cells express EGFP, i.e. larval, pupal, and adult eyes, as well as the ocelli (Drosophila).

In Drosophila we have also tested constructs 3×P3-EYFP and 3×P3-ECFP for their use as universal markers. Both 3×P3-EYFP and 3×P3-ECFP work excellently like 3×P3-EGFP. Moreover, 3×P3-EYFP and 3×P3-ECFP represent an ideal pair of markers that can easily be distinguished by specific filter sets, thus comprising independent and separable markers for identifying animals transgenic for different constructs.

All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of making a transgenic insect comprising the steps of:
   (a) introducing into a genome of an insect a polytropic vector functional in nondipteran species and comprising a genetic construct comprising a transcriptional regulatory element operably linked to a heterologous gene encoding a marker, wherein the element comprises a binding site selected from a group consisting of a Pax-6 binding site and a Glass binding site and drives sufficient expression of the marker in insect genera transgenic of the construct to allow visual detection of the marker in photoreceptive cells or organs across said genera, and
   (b) selecting for transgenesis by visually detecting the marker in a photoreceptive cell or organ of the insect.

2. The method according to claim 1, wherein the vector comprises a polytropic transposon.

3. The method according to claim 1, wherein the vector comprises a pantropic transposon.

4. The method according to claim 1, wherein the vector comprises a polytropic retrovirus.

5. The method according to claim 1, wherein the vector comprises a pantropic retrovirus.

6. The method according to claim 1, wherein the construct comprises first and second regions homologous to corresponding portions of the genome and the introducing step comprises homologously recombining the construct with the genome.

7. The method according to claim 1, wherein the introducing step comprises non homologously recombining the construct with the genome.

8. The method according to claim 1, wherein the element comprises a Glass binding site.

9. The method according to claim 1, wherein the element comprises a Pax-6 binding site.

10. The method according to claim 1, wherein the element comprises a plurality of Pax6 binding sites.

11. The method according to claim 1, wherein the element comprises a plurality of Pax-6 binding sites and said Pax6 binding sites are P3 sites.

12. The method according to claim 1, wherein the element comprises a plurality of Pax-6 binding sites and said Pax-6 binding sites are Paired Domain binding sites.

13. The method according to claim 1, wherein the element comprises a plurality of Pax-6 binding sites and said Pax6 binding sites comprise twin-of-eyeless (TOY) binding sites.

14. The method according to claim 1, wherein the element comprises a plurality of Pax-6 binding sites, and said plurality is from 3 to 9.

15. The method according to claim 1, wherein the marker is a fluorescent protein.

16. The method according to claim 1, wherein the marker is a fluorescent protein and said fluorescent protein is a green fluorescent protein.

17. The method according to claim 1, wherein the vector and element are functional in an insect selected from the group consisting of Lepidoptera, Hymenoptera, Coleoptera, Neuroptera, Hemiptera, Isoptera, Dictyoptera, and Orthoptera.

18. The method according to claim 1, wherein the vector and element are functional in Lepidoptera, Hymenoptera, Coleoptera, Neuroptera, Hemiptera, Isoptera, Dictyoptera, and Orthoptera species.

19. The method according to claim 1, wherein the vector and element are functional in non-dipteran insects.

20. A nonhuman transgenic insect made by the method of claim 1.

21. A polytropic vector functional in nondipteran insect species and comprising a transcriptional regulatory element operably linked to a heterologous gene encoding a marker, wherein the element drives sufficient expression of the marker in insect genera, including a non-dipteran insect, transgenic of the construct to allow visual detection of the marker in photoreceptive cells or organs.

22. The vector according to claim 21, wherein the marker is the only visually detectable indicator of transgenesis encoded by the vector.

23. An insect cell stably transformed with the vector according to claim 21, or a progeny of said cell.

24. A nonhuman insect stably transformed with the vector according to claim 21, or a progeny of said insect, wherein expression of the marker is sufficient to allow visual detection of the marker in photoreceptive cells or organs of the insect.

25. The method according to claim 1, wherein the genetic construct is introduced into a vector selected from the group consisting of Himar1, piggyBac, Hermes, hobo, minos and mariner.

26. The method according to claim 1, wherein the insect is a non-dipteran insect.

27. The method according to claim 1, wherein the insect is selected from the group consisting of Lepidoptera, Hymenoptera, Coleoptera, Neuroptera, Hemiptera, Isoptera, Dictyoptera, and Orthoptera.

28. The method according to claim 1, wherein the insect is Drosophila.

29. The method according to claim 1, wherein the insect is Tribolium.

30. The method according to claim 1, wherein the marker is detected in live, intact insects.

31. The vector according to claim 21, wherein said transcriptional regulatory element and said heterologous gene are introduced into a vector selected from the group consisting of Himar1, piggyBac, Hermes, hobo, minos and mariner.

32. An insect according to claim 24, wherein the insect is a non-dipteran insect.

33. An insect according to claim 24, wherein the insect is selected from the group consisting of Lepidoptera, Hymenoptera, Coleoptera, Neuroptera, Hemiptera, Isoptera, Dictyoptera, and Orthoptera.

34. An insect according to claim 24, wherein the insect is Drosophila.

35. An insect according to claim 24, wherein the insect is Tribolium.

36. A method of making a transgenic insect comprising the steps of:
   (a) introducing into a genome of an insect a polytropic vector functional in nondipteran species and comprising a genetic construct comprising a transcriptional regulatory element operably linked to a heterologous gene encoding a marker, wherein the element comprises a binding site selected from a group consisting of a Pax-6 binding site and a Glass binding site and drives sufficient expression of the marker in insect genera transgenic of the construct to allow visual detection of the marker in photoreceptive cells or organs across said genera, and (b) selecting for transgenesis by visually detecting the marker in a photoreceptive cell or organ of the insect;

wherein the marker is a fluorescent protein, and wherein the genetic construct is introduced into a vector selected from the group consisting of Himar1, piggyBac, Hermes, hobo, minos and mariner.

37. A polytropic vector functional in nondipteran insect species and comprising a transcriptional regulatory element operably linked to a heterologous gene encoding a marker, wherein the element drives sufficient expression of the marker in insect genera transgenic of the construct to allow visual detection of the marker in photoreceptive cells or organs, wherein the marker is a fluorescent protein, and wherein said transcriptional regulatory element and said heterologous gene are introduced into a vector selected from the group consisting of Himar1, piggyBac, Hermes, hobo, minos and mariner.

38. The vector according to claim 21, wherein the genera include a plurality of taxonomic families.

39. The vector according to claim 21, wherein the genera include a plurality of taxonomic orders.

40. The vector according to claim 21, wherein the genera include the families Drosophilidae, Calliphoridae and Culicidae.

41. The vector according to claim 21, wherein the genera include the orders Dipetera, Lepidoptera and Coleoptera.

* * * * *

SEQUENCE LISTING

```
<160> NUMBER OF SEQ ID NOS:  44

<210> SEQ ID NO 1
<211> LENGTH: 11
<212> TYPE: DNA
<213> ORGANISM: Artificial Sequence
<220> FEATURE:
<223> OTHER INFORMATION: Description of Artificial Sequence: Synthetic
      DNA
<221> NAME/KEY: variation
<222> LOCATION: (6)
<223> OTHER INFORMATION: n signifies any nucleotide

<400> SEQUENCE: 1
taatynratt a                                                          11

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 2
tcgagcccag tggaaaccct tgaaatgcct ttaag                                35

<210> SEQ ID NO 3
<211> LENGTH: 35
<212> TYPE: DNA
```

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: Synthetic DNA

<400> SEQUENCE: 3
tcgacttaaa ggcatttcaa gggtttccac tgggc                         35

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Synthetic DNA

<400> SEQUENCE: 4
gatcccagtg gaaaccttg aaatgccttt aa                             32

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: Synthetic DNA

<400> SEQUENCE: 5
gatcttaaag gcatttcaag ggtttccact gg                            32

<210> SEQ ID NO 6
<211> LENGTH: 43
<212> TYPE: DNA
<213> ORGANISM: Artificial Sequence
<220> FEATURE:
<223> OTHER INFORMATION: Description of Artificial Sequence: Synthetic DNA

<400> SEQUENCE: 6
tcgagacacc cagtggaaac ccttgaaatg cctttaacta ttg                43

<210> SEQ ID NO 7
<211> LENGTH: 43
<212> TYPE: DNA
<213> ORGANISM: Artificial Sequence
<220> FEATURE:
<223> OTHER INFORMATION: Description of Artificial Sequence: Synthetic DNA

<400> SEQUENCE: 7
tcgacaatag ttaaaggcat ttcaagggtt tccactgggt gtc                43

<210> SEQ ID NO 8
<211> LENGTH: 44
<212> TYPE: DNA
<213> ORGANISM: Artificial Sequence
<220> FEATURE:
<223> OTHER INFORMATION: Description of Artificial Sequence: Synthetic DNA

<400> SEQUENCE: 8
tcgagacacc cagtggaaac ccttgaaatg cctttaactc agtg               44

<210> SEQ ID NO 9
<211> LENGTH: 44
<212> TYPE: DNA
<213> ORGANISM: Artificial Sequence

```
<220> FEATURE:
<223> OTHER INFORMATION: Description of Artificial Sequence: Synthetic
      DNA

<400> SEQUENCE: 9
tcgacactga gttaaaggca tttcaagggt ttccactggg tgtc                    44

<210> SEQ ID NO 10
<211> LENGTH: 43
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 10
tcgagacacc cagtggaaac ccttgaaatg cctttttcaga ttg                    43

<210> SEQ ID NO 11
<211> LENGTH: 43
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 11
tcgacaatct gaaaaggcat ttcaagggtt tccactgggt gtc                     43

<210> SEQ ID NO 12
<211> LENGTH: 11
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 12
taatcagatt a                                                        11

<210> SEQ ID NO 13
<211> LENGTH: 11
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 13
taattgaatt t                                                        11

<210> SEQ ID NO 14
<211> LENGTH: 11
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 14
taattgggtt a                                                        11

<210> SEQ ID NO 15
<211> LENGTH: 11
<212> TYPE: DNA
<213> ORGANISM: Artificial Sequence
<220> FEATURE:
```

<223> OTHER INFORMATION: Description of Artificial Sequence: Synthetic
      DNA

<400> SEQUENCE: 15
taatccaatt c                                                              11

<210> SEQ ID NO 16
<211> LENGTH: 11
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 16
taattggctc a                                                              11

<210> SEQ ID NO 17
<211> LENGTH: 11
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 17
taatccaatt g                                                              11

<210> SEQ ID NO 18
<211> LENGTH: 11
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 18
aaattgaatt a                                                              11

<210> SEQ ID NO 19
<211> LENGTH: 11
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 19
taatttaatt t                                                              11

<210> SEQ ID NO 20
<211> LENGTH: 11
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 20
taatatgatt a                                                              11

<210> SEQ ID NO 21
<211> LENGTH: 11
<212> TYPE: DNA
<213> ORGANISM: Artificial Sequence
<220> FEATURE:
<223> OTHER INFORMATION: Description of Artificial Sequence: Synthetic

```
      DNA

<400> SEQUENCE: 21
taattgaatt a                                                               11

<210> SEQ ID NO 22
<211> LENGTH: 11
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 22
taatgtaatt a                                                               11

<210> SEQ ID NO 23
<211> LENGTH: 11
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 23
taattcaatt a                                                               11

<210> SEQ ID NO 24
<211> LENGTH: 16
<212> TYPE: DNA
<213> ORGANISM: Artificial Sequence
<220> FEATURE:
<223> OTHER INFORMATION: Description of Artificial Sequence: Synthetic
      DNA
<221> NAME/KEY: variation
<222> LOCATION: (2)..(15)
<223> OTHER INFORMATION: n signifies any nucleotide

<400> SEQUENCE: 24
annttcacgc atgant                                                          16

<210> SEQ ID NO 25
<211> LENGTH: 16
<212> TYPE: DNA
<213> ORGANISM: Artificial Sequence
<220> FEATURE:
<223> OTHER INFORMATION: Description of Artificial Sequence: Synthetic
      DNA
<221> NAME/KEY: variation
<222> LOCATION: (2)..(15)
<223> OTHER INFORMATION: n signifies any nucleotide

<400> SEQUENCE: 25
annttcacgc ttcant                                                          16

<210> SEQ ID NO 26
<211> LENGTH: 16
<212> TYPE: DNA
<213> ORGANISM: Artificial Sequence
<220> FEATURE:
<223> OTHER INFORMATION: Description of Artificial Sequence: Synthetic
      DNA
<221> NAME/KEY: variation
<222> LOCATION: (2)..(15)
<223> OTHER INFORMATION: n signifies any nucleotide

<400> SEQUENCE: 26
annttcacgc atcant                                                          16
```

```
<210> SEQ ID NO 27
<211> LENGTH: 16
<212> TYPE: DNA
<213> ORGANISM: Artificial Sequence
<220> FEATURE:
<223> OTHER INFORMATION: Description of Artificial Sequence: Synthetic
      DNA
<221> NAME/KEY: variation
<222> LOCATION: (2)..(15)
<223> OTHER INFORMATION: n signifies any nucleotide

<400> SEQUENCE: 27
annttcacgc ttgant                                                    16

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 28
atgctcagtg aatgttcatt ga                                             22

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 29
tcaatgaaca ttcactgagc at                                             22

<210> SEQ ID NO 30
<211> LENGTH: 10
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 30
tgcatcgagg                                                           10

<210> SEQ ID NO 31
<211> LENGTH: 11
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 31
atgttcactg a                                                         11

<210> SEQ ID NO 32
<211> LENGTH: 13
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 32
```
caattagtca cgc                                                            13

<210> SEQ ID NO 33
<211> LENGTH: 13
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 33
caattattca cgc                                                            13

<210> SEQ ID NO 34
<211> LENGTH: 13
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 34
caattagtca cgg                                                            13

<210> SEQ ID NO 35
<211> LENGTH: 13
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 35
caattattca cgg                                                            13

<210> SEQ ID NO 36
<211> LENGTH: 13
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 36
cgattagtca cgc                                                            13

<210> SEQ ID NO 37
<211> LENGTH: 13
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 37
cgattattca cgc                                                            13

<210> SEQ ID NO 38
<211> LENGTH: 13
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 38

```
cgattagtca cgg                                                          13

<210> SEQ ID NO 39
<211> LENGTH: 13
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 39
cgattattca cgg                                                          13

<210> SEQ ID NO 40
<211> LENGTH: 10
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 40
taattgatta                                                              10

<210> SEQ ID NO 41
<211> LENGTH: 10
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 41
taatcgatta                                                              10

<210> SEQ ID NO 42
<211> LENGTH: 10
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 42
taatcaatta                                                              10

<210> SEQ ID NO 43
<211> LENGTH: 10
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 43
taattaatta                                                              10

<210> SEQ ID NO 44
<211> LENGTH: 40
<212> TYPE: DNA
<213> ORGANISM: Artificial Sequence
<220> FEATURE:
<223> OTHER INFORMATION: Description of Artificial Sequence: Synthetic
      DNA
```

-continued

<400> SEQUENCE: 44
ggatccaagc ttatcgattt cgaaccctcg accgccggag        40